(12) United States Patent
Gritzbach et al.

(10) Patent No.: US 7,574,371 B2
(45) Date of Patent: Aug. 11, 2009

(54) MEDICAL DIAGNOSIS MANAGEMENT SYSTEM

(75) Inventors: Ralph Gritzbach, Erlangen (DE); Juergen Heller, Spardorf (DE)

(73) Assignee: Siemens AG, Munich (DE)

( * ) Notice: Subject to any disclaimer, the term of this patent is extended or adjusted under 35 U.S.C. 154(b) by 990 days.

(21) Appl. No.: 09/988,455

(22) Filed: Nov. 20, 2001

(65) Prior Publication Data

US 2002/0062068 A1 May 23, 2002

(30) Foreign Application Priority Data

Nov. 22, 2000 (DE) .................... 100 57 781

(51) Int. Cl.
*A61B 5/00* (2006.01)
(52) U.S. Cl. .............................. 705/3; 345/418; 379/38; 600/300; 600/301; 600/437; 600/483; 600/508; 600/509; 600/513; 600/515; 600/595; 604/151; 604/66; 705/2; 709/230; 725/116
(58) Field of Classification Search ...................... 705/3, 705/1, 2; 709/230; 600/300, 301, 515, 513, 600/509, 483, 437, 595, 508, 484; 725/116; 379/38; 345/418; 604/151, 66
See application file for complete search history.

(56) References Cited

U.S. PATENT DOCUMENTS

| | | | | |
|---|---|---|---|---|
| 3,986,498 | A * | 10/1976 | Lewis | 600/508 |
| 4,259,548 | A * | 3/1981 | Fahey et al. | 379/38 |
| 4,838,275 | A * | 6/1989 | Lee | 600/483 |
| 5,038,800 | A * | 8/1991 | Oba | 600/509 |
| 5,339,821 | A * | 8/1994 | Fujimoto | 600/513 |
| 5,375,604 | A * | 12/1994 | Kelly et al. | 600/484 |
| 5,434,611 | A * | 7/1995 | Tamura | 725/116 |
| 5,438,607 | A * | 8/1995 | Przygoda et al. | 379/38 |
| 5,441,047 | A * | 8/1995 | David et al. | 600/483 |
| 5,544,649 | A * | 8/1996 | David et al. | 600/301 |

(Continued)

FOREIGN PATENT DOCUMENTS

DE 198 08 616 A1 9/1998

(Continued)

OTHER PUBLICATIONS

Derwent WPI Abstract No. 1998-497108 (for DE 198 08 616 A1).

*Primary Examiner*—C. Luke Gilligan
*Assistant Examiner*—Dilek B Cobanoglu
(74) *Attorney, Agent, or Firm*—Schiff Hardin LLP

(57) ABSTRACT

A computerized medical diagnosis management system includes a central computer system comprising a data processor; at least one data interface operatively coupled to the data processor and configured to receive data from two or more diagnosis instruments, wherein each diagnosis instrument is configured for displaying measurement data and/or diagnosis data on a local monitor; an input unit operatively coupled to the data processor and configured to select a diagnosis instrument from the two or more diagnosis instruments and to generate a control code for the selected diagnosis instrument, when a control instruction is entered through the input unit; and a display unit operatively coupled to the data processor and configured to display the received data simultaneously or successively, wherein the data interface automatically forwards the control code to the selected diagnosis instrument. A method and a computer program product for using the system.

14 Claims, 1 Drawing Sheet

U.S. PATENT DOCUMENTS

| | | | | |
|---|---|---|---|---|
| 5,553,609 | A | * | 9/1996 | Chen et al. .................. 600/301 |
| 5,558,638 | A | * | 9/1996 | Evers et al. ................... 604/66 |
| 5,576,952 | A | * | 11/1996 | Stutman et al. ............. 600/300 |
| 5,619,991 | A | * | 4/1997 | Sloane ....................... 600/300 |
| 5,640,953 | A | * | 6/1997 | Bishop et al. ............... 600/300 |
| 5,687,734 | A | * | 11/1997 | Dempsey et al. ............ 600/509 |
| 5,810,747 | A | * | 9/1998 | Brudny et al. ............... 600/595 |
| 5,842,173 | A | * | 11/1998 | Strum et al. .................... 705/1 |
| 5,912,656 | A | * | 6/1999 | Tham et al. ................. 345/418 |
| 5,913,197 | A | * | 6/1999 | Kameda ......................... 705/3 |
| 5,931,791 | A | * | 8/1999 | Saltzstein et al. ........... 600/513 |
| 5,987,519 | A | * | 11/1999 | Peifer et al. ................. 709/230 |
| 6,003,072 | A | | 12/1999 | Gerritsen et al. |
| 6,006,191 | A | * | 12/1999 | DiRienzo ....................... 705/2 |
| 6,024,699 | A | * | 2/2000 | Surwit et al. ................. 600/300 |
| 6,402,691 | B1 | * | 6/2002 | Peddicord et al. ........... 600/300 |
| 6,416,471 | B1 | * | 7/2002 | Kumar et al. ................ 600/300 |
| 6,436,040 | B1 | * | 8/2002 | Collamore et al. .......... 600/437 |
| 6,579,231 | B1 | * | 6/2003 | Phipps ........................ 600/300 |
| 2002/0013551 | A1 | * | 1/2002 | Zaitsu et al. ................. 604/151 |
| 2002/0133087 | A1 | * | 9/2002 | Bayer et al. ................. 600/515 |
| 2003/0074227 | A1 | * | 4/2003 | Yu .................................. 705/3 |

FOREIGN PATENT DOCUMENTS

JP            08-28066 A      10/1996

* cited by examiner

MEDICAL DIAGNOSIS MANAGEMENT SYSTEM

BACKGROUND OF THE INVENTION

1. Field of the Invention

The invention relates to medical diagnosis management technology. In particular, the invention relates to a system for optimizing medical diagnosis instrument management.

2. Related Art

In a hospital or other medical treatment facility, a plurality of medical diagnosis instruments are generally available, each of which is operated by a technician assigned to the relevant diagnosis instrument. Examples of such diagnosis instruments include computer tomographs, MRI tomographs, X-ray examination systems, angiography systems, or other large medical equipment. The diagnosis instruments also require the presence of a doctor, sometimes continually, and sometimes only when necessary for more complex examinations, in order to draw conclusions regarding the further course of the examination from the diagnosis data that has been obtained.

This takes up a great deal of the doctor's time, especially when the diagnosis instruments in a clinic are spread over a plurality of locations, and long distances therefore have to be covered to travel from one diagnosis instrument to another. High costs in terms of a doctor's time are also entailed whenever a diagnosis instrument, at which the doctor is already present, breaks down or needs to be recalibrated, or if another patient's examination needs to be immediately fit in due to an emergency.

SUMMARY

The invention provides a system and a method with which the working procedure in medical diagnosis may be improved and which, in particular, may contribute to the reduction of working costs.

The invention provides a computerized medical diagnosis management system that includes a central computer system comprising a data processor; at least one data interface operatively coupled to the data processor and configured to receive data from two or more diagnosis instruments, wherein each diagnosis instrument is configured for displaying measurement data and/or diagnosis data on a local monitor; an input unit operatively coupled to the data processor and configured to select a diagnosis instrument from the two or more diagnosis instruments and to generate a control code for the selected diagnosis instrument when a control instruction is entered through the input unit; and a display unit operatively coupled to the data processor and configured to display the received data simultaneously or successively, wherein the data interface automatically forwards the control code to the selected diagnosis instrument.

The invention further provides a computerized method for managing two or more medical diagnosis instruments by receiving at a central computer system measurement data and/or diagnosis data from the diagnosis instruments in real time; presenting to an operator the measurement data and/or diagnosis data simultaneously or successively on a display unit operatively coupled to a data processor of the central computer system; selecting a diagnosis instrument from the plurality of diagnosis instruments when the operator enters an input into the data processor; converting the entered input into a control code for the selected diagnosis instrument; and forwarding the control code in real time from the central computer system to the selected diagnosis instrument.

The invention further provides a computer program product including a computer-readable storage medium on which a program code is stored, wherein the computer program product further includes program code for causing a central computer system comprising a data processor to receive measurement data and/or diagnosis data from two or more diagnosis instruments in real time; program code for causing at least one data interface to receive data from the diagnosis instruments, wherein the diagnosis instruments are configured for displaying measurement data and/or diagnosis data on a monitor; program code for causing an input unit to select a diagnosis instrument and generate a control code for the selected diagnosis instrument when a control instruction is entered through the input unit; program code for causing a display unit operatively coupled to the data processor to display the received data simultaneously or successively; and program code for causing the data interface to automatically forward the control code to the selected diagnosis instrument.

BRIEF DESCRIPTION OF THE DRAWING

Features and details of the invention can be found in the illustrative embodiments of the invention which are described below with reference to the drawing, in which.

DETAILED DESCRIPTION OF THE INVENTION

Figure 1:
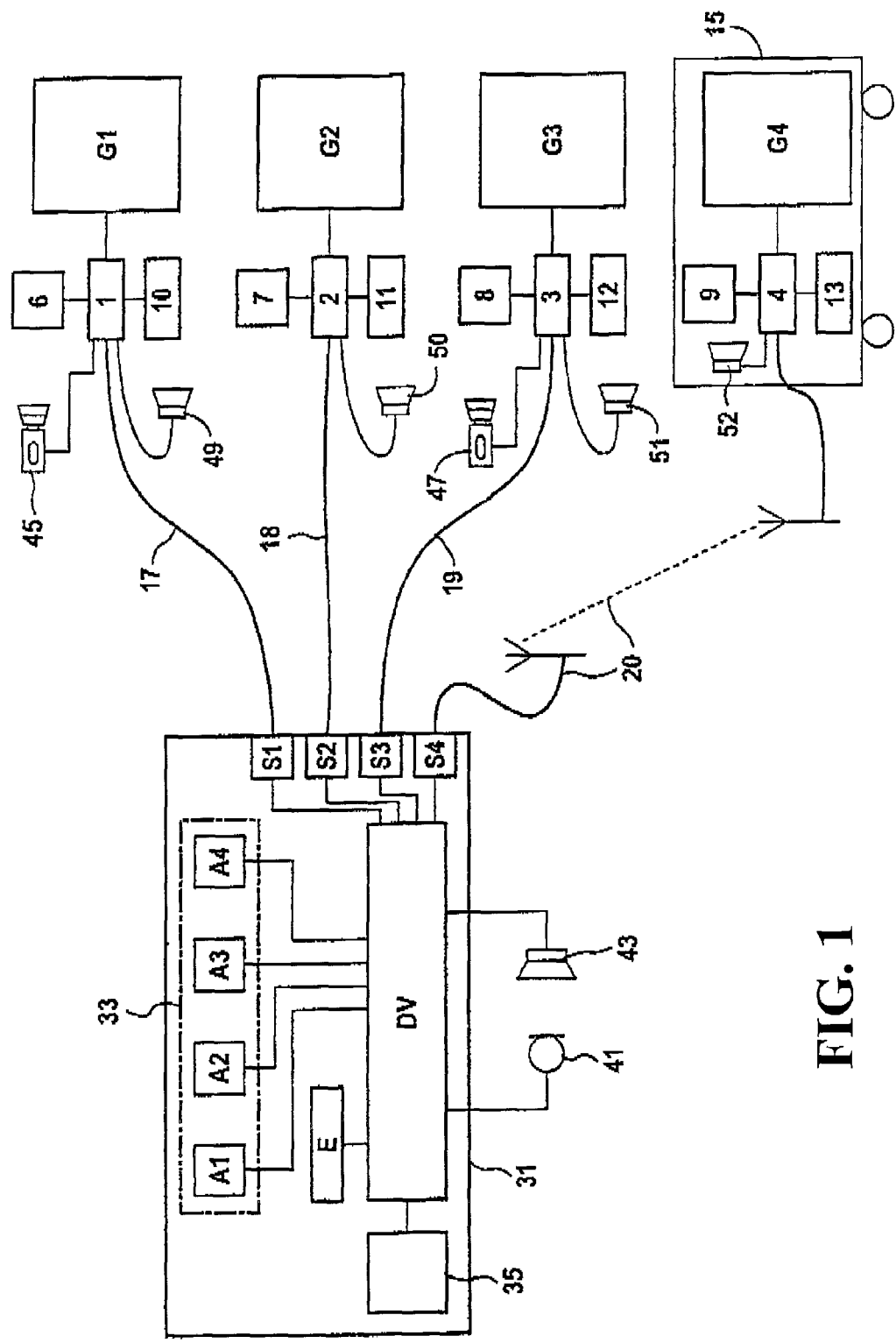
FIG. 1 shows a schematic of a diagnosis management system according to the invention and associated remote diagnosis instrument systems.

The invention makes the presence of a doctor on site at the respective medical diagnosis instruments no longer necessary in order to answer application questions during the examination, or to obtain extra information by initiating further examination steps. Instead, it is sufficient for the doctor to be present at the diagnosis management system. From there, the doctor can observe the examinations taking place at the diagnosis instruments and, should the need arise, may intervene in the examination procedure at the diagnosis instruments from the—possibly very distant—site of the diagnosis management system. The doctor may thus function simultaneously as a central supervisor for a plurality of medical diagnosis instruments, without having to be present at each of them. "Doctor" means any professional that is qualified or authorized to make an assessment or diagnosis, or otherwise act in a supervisory manner, based on data received from the medical diagnosis instrument(s).

It may then be sufficient for staff who have only a lower level of training to be present on site at the diagnosis instruments. Their activity can be supervised by the doctor and, should the need arise, the doctor may even take control of one of the medical diagnosis instruments by remote control, and then continue the examination himself or herself according to his or her control instructions. If an interruption in the examination procedure occurs at one of the medical diagnosis instruments, this does not actually cause the doctor to become inactive since the doctor can still communicate with other diagnosis instruments assigned to the diagnosis management system.

In particular, the diagnosis management system according to the invention can hence be connected, preferably simultaneously, to a plurality of medical diagnosis instruments. As few as 2-3 diagnostic instruments may be connected, preferably four or more, but the number is not particularly limited.

"Diagnosis instrument" means any equipment or machine used for medical diagnosis, evaluation, or analysis. In particular, suitable diagnosis instruments include medical examination instruments for imaging, in particular large expensive instruments. For example, the diagnosis management system may be connected to a computer tomograph, an MRI tomograph, an angiographic X-ray machine, an X-ray examination machine, a conventional station for taking X-rays, and/or another medical examination machine. Different types of diagnosis instruments may be in communication with the system. These various diagnosis instruments generally use different data formats for the diagnosis data. Preferably, software that is run on the central diagnosis management system, as a computer system, is configured in such a way that the different formats can be standardized and presented in a standard format on the display unit to a doctor present at the system.

The medical diagnosis instruments connected to the system need not necessarily be installed at fixed locations. Instead, the diagnosis instruments, or one of the diagnosis instruments, may be arranged on a mobile platform, for example in a motor vehicle, and may even be used outside a hospital, for example for screening programs.

Should the need arise, the on-site technician at the diagnosis instrument can connect to the doctor working at the central device.

The data received from the medical diagnosis instruments contains measurement data and/or diagnosis data, for example image data. It may also contain application data and/or control data.

According to a preferred embodiment, the display unit displays the data in the same way as the monitor that is locally available to the respective medical diagnosis instrument. The local monitor may be represented on the display unit. For its part, the display unit may have a plurality of monitors and/or be designed as a split screen.

This provides the advantage that the doctor—especially when problems arise—can establish communication in a particularly efficient way with the technician working on site, since they are both using the same data.

According to another preferred embodiment, the input unit, the data processor, and optionally the display unit of the diagnosis management system are designed so that the control instruction can be input in such a way that a local operating procedure at the medical diagnosis instrument can be replicated.

For example, the display unit of the diagnosis management system may replicate an operating console of the diagnosis instrument. For example, the doctor may operate the operating console replicated on the display unit, in a virtual fashion, by using a computer mouse or a joystick.

The replicated operating console allows the doctor to control the examination at the diagnosis instrument in real time in the same way as the technician working on site. This facilitates collaboration of the doctor with the on-site technician.

In order to facilitate communication between the doctor and the on-site technician, the central computer system may also be provided with an acoustic input device in order to pick up a voice signal spoken at the site of the input unit. In this case, the data processing system preferably sends the voice signal to the data interface of the respectively selected medical diagnosis instrument. This ensures that the doctor's spoken instructions reach the correct diagnosis instrument in each case. In the same way, the central computer system may be provided with an acoustic output device, for example a loudspeaker, to which voice signals from the technician at the respectively selected medical diagnosis instrument are sent via the data interface, so that the doctor can listen to what is being said at the diagnosis instrument.

It is also preferable to provide the diagnosis management system with at least one camera that is installed at the site of one of the diagnosis instruments in order to supervise the working procedure there, the associated data interface being designed to record image data from the camera. This allows the doctor carrying out centralized supervision to observe not only the control instructions and actions implemented at the respective diagnosis instrument by the technician working on site, but also the way in which the technician configures the overall working procedure, e.g., the way in which a patient is being supported.

Preferably, the data interfaces are designed as Internet interfaces. The data communication can take place via an intranet, the Internet, or another data network. Some of the data transfer may also take place using a wireless system, in particular so that the central device can be connected to a mobile medical diagnosis instrument.

The method of the invention is suitable, in particular, for operating the diagnosis management system according to the invention. The configurations relating to the diagnosis management system apply similarly to the method.

The transmitted data contains diagnosis and/or measurement data, for example image data, application data, and/or control data.

Preferably, the data from one of the medical diagnosis instruments is visualized on the display unit in the same way as on the monitor that is locally available to the relevant medical diagnosis instrument.

The operator is preferably a doctor or another highly qualified, medically trained person suitable for fulfilling a supervisory function.

In the method, a voice signal from the operator is preferably also picked up and sent by the central computer system to the site of the selected medical diagnosis instrument.

According to a particularly preferred embodiment of the invention, stored data, which was earlier saved at one of the medical diagnosis instruments, is transmitted to the central computer system and presented on the display unit. This makes it possible for the operator to carry out two successive interventions in the examination procedure at different diagnosis instruments, even though the examination processes are taking place simultaneously and the diagnosis data has therefore been made available to the operator at the same time.

The invention also relates to a computer program with which the method according to the invention can be carried out when it is run on a computer, in particular on a computer of the central device of the diagnosis management system according to the invention.

In this context, the invention also relates to a computer program product, comprising a computer-readable storage medium on which a program code is stored, with which the method according to the invention can be carried out when the program code is run on a computer.

An exemplary embodiment of a system and method according to the invention is explained in more detail below with the aid of FIG. 1.

FIG. 1 shows four medical diagnosis instruments G1, G2, G3, G4, each of which is respectively provided with a local data processing system 1, 2, 3, 4, e.g., a personal computer, as well as a local monitor 6, 7, 8, 9, and a local input unit 10, 11, 12, 13, e.g., a keyboard, a mouse and/or a joystick. The local data processing systems 1, 2, 3, 4 are used for local evaluation and presentation of the diagnosis or measurement data obtained from the respective medical diagnosis instrument G1, G2, G3, G4, to a locally present technician.

Medical diagnosis instrument G4 is arranged together with data processing system 4, monitor 9, and input unit 13 on a mobile platform 15, e.g., in a motor vehicle for examination purposes.

Medical diagnosis instruments G1, G2, G3, G4 are connected via respective data connections 17, 18, 19, 20, respectively, to a central computer system 31. The data connections 17, 18, 19, 20 may be any data communication means, e.g., cable or wireless.

The central computer system 31 has four data interfaces S1, S2, S3, S4, which are each connected to one of the data connections 17, 18, 19, and 20, respectively. Data interfaces S1, S2, S3, S4 may be embodied in hardware form as four modules, each with an outgoing data connection, or in software form as a single module with only one outgoing line, which is connected to the different medical diagnosis instruments G1, G2, G3, G4, in accordance with its addressing, as is the case, e.g., with conventional Internet connections.

The central computer system 31 has a data processor DV that communicates with the data interfaces S1, S2, S3, S4, and that is provided with an input unit E, e.g., a computer keyboard, a mouse and/or a joystick, as well as a display unit 33. The display unit 33 comprises either at least four separate display devices A1, A2, A3, and A4 for displaying data from the medical diagnosis instruments G1, G2, G3, and G4 or only a single visual output device, whose monitor is divided into four parts as a split screen (not shown).

The central computer system 31 also has a memory 35 that is connected to the data processor DV, and wherein incoming data from the medical diagnosis instruments G1, G2, G3, G4 can be temporarily saved.

The central computer system 31 is also provided with a microphone or acoustic input device 41, which can be used to transmit the doctor's voice to the site of the respectively selected medical diagnosis instrument G1, G2, G3, G4, via the respective data interface S1, S2, S3, S4. Corresponding loudspeakers 49, 50, 51, 52 are provided at the medical diagnosis instruments G1, G2, G3, G4.

Further, the central computer system 31 is connected to a loudspeaker or acoustic output device 43, using which the doctor can hear the voice of the technician at the selected medical diagnosis instrument G1, G2, G3, G4 in combination with a microphone (not shown) present at each diagnosis instrument.

Cameras 45 and 47 are also respectively installed at the site of the medical diagnosis instruments G1, G3, and their image data can be delivered via the associated data interface S1 or S3, respectively, to the central computer system 31, where the image data can be presented on the display unit 33. In this way, the doctor can fully observe the examination procedure taking place on site.

The method according to the invention is explained below with reference to the following Example.

EXAMPLE

A local technician is present at each of the medical diagnosis instruments G1, G2, G3, G4, where a doctor is carrying out an examination on a patient. The examinations take place simultaneously. The local technician follows the respective examination on his or her local monitor 6, 7, 8, 9. The data from diagnosis instruments G1, G2, G3, G4 is transmitted in real time to the central computer system 31. There, the data is presented simultaneously on respectively assigned display devices A1, A2, A3, A4, so that a doctor present at the central computer system 31 can see the data. The doctor supervises the examinations taking place at remote locations on medical diagnosis instruments G1, G2, G3, G4. Should the doctor decide that it is necessary to intervene in one of the examinations, then the doctor uses the input unit E to select corresponding medical diagnosis instrument G1, G2, G3, or G4 for intervention.

When the doctor selects one of the medical diagnosis instruments G1, G2, G3, G4, an acoustic link from the doctor to the local technician is automatically established by means of acoustic input device 41 and acoustic output device 43. Further, when the doctor selects instrument G1 or G3, the image data from respective camera 45 or 47 optionally present on site is displayed to the doctor. The selection also ensures that the doctor can intervene in the operating procedure or examination process at the selected medical diagnosis instrument G1, G2, G3, or G4 by remote control via the corresponding data interface S1, S2, S3, or S4. An input entered by the doctor using the input unit E is converted by the data processing system DV into a control code for the selected medical diagnosis instrument G1, G2, G3, or G4. The control code is then forwarded in real time to the selected medical diagnosis instrument G1, G2, G3, or G4. In this way, the doctor is virtually present at the respective examination, i.e., the doctor may not only work by means of online diagnosis, but may also intervene actively in the events on site. The working costs are reduced in comparison with a practice in which the doctor successively visits in person the medical diagnosis instruments G1, G2, G3, G4.

While embodiments of the invention have been described above, those embodiments illustrate but do not limit the invention. Adaptations and variations of those embodiments are within the scope of the invention as set forth in the following claims.

We claim:

1. A computerized medical imaging examination management system allowing a central operator to monitor and control a predetermined number of medical examination imaging instruments in real time, comprising:

a central computer system comprising a data processor;

a predetermined number of data interfaces each operatively coupled to the data processor and each data interface is configured to receive data from a respective medical examination imaging instrument in real time, wherein each imaging instrument is located at a different remote patient site and configured for displaying imaging data on a local monitor allowing a local operator to monitor the imaging instrument at a patient site during a patient's examination;

a display unit operatively coupled to the data processor and configured to represent each local monitor simultaneously, wherein the display unit is further configured to display the imaging data in the same way as the respective local monitor, wherein a number of represented local monitors corresponds to the predetermined number of imaging instruments, and wherein the simultaneous representations of local monitors on the display unit allow the central operator to monitor and control the imaging instruments during patient examinations; and an input unit operatively coupled to the data processor and configured to allow the central operator to select an imaging instrument from the imaging instruments represented on the display unit, and to generate a control code for the selected imaging instrument, when a control instruction for actively controlling the selected imaging instrument is entered by the central operator through the input unit to enable active intervention in real time by the central operator during a patient's imaging examination, wherein the data interface automatically forwards the control code to the selected imaging instrument.

2. The system as claimed in claim 1, wherein the data interface is one of
two or more hardware modules each operatively coupled via a separate data communications line to an imaging instrument, and
a software module configured to access the imaging instruments based on addressing information for each imaging instrument.

3. The system as claimed in claim 1, wherein the data interface is configured as an Internet interface.

4. The system as claimed in claim 1, wherein the system is configured to receive data from at least two imaging instruments that transmit data in dissimilar formats.

5. The system as claimed in claim 1, wherein the system is configured to receive data from an imaging instrument mounted on a mobile platform.

6. The system as claimed in claim 1, wherein the system is configured to replicate an operating console of the imaging instrument in response to the control instruction.

7. The system as claimed in claim 1, further comprising an acoustic input device configured to pick up a voice signal spoken at the site of the input unit of the imaging management system, wherein the data processor sends the voice signal to a selected medical imaging instrument.

8. The system as claimed in claim 1, wherein the system is configured to receive image data from at least one camera installed at the site of one of the imaging instruments, and wherein the data interface is configured for recording the image data.

9. A computerized method for managing a predetermined number of medical examination imaging instruments located at remote patient sites in real time, comprising:
receiving at a central computer system via a plurality of data interfaces imaging data from the remotely located imaging instruments in real time, wherein each data interface is assigned to one of the imaging instruments, and wherein each imaging instrument is located at a different remote patient site and configured for displaying imaging data on a local monitor allowing a local operator to monitor the imaging instrument at a patient site during a patient's examination;
simultaneously displaying on a display unit operatively coupled to a data processor of the central computer system a number of representations of the local monitors to allow the central operator to monitor and control the remotely located imaging instruments in real time during patient examinations, wherein the number of represented local monitors corresponds to the predetermined number of imaging instruments, and wherein the display unit displays the imaging data in the same way as the respective local monitor;
selecting an imaging instrument from the imaging instruments represented on the display unit for active control by the central operator when the central operator enters an input into the data processor;
converting the entered input into a control code for the selected imaging instrument to enable active intervention by the central operator in real time during a patient's examination;
forwarding the control code in real time from the central computer system to the selected imaging instrument; and
controlling the imaging instrument in real time via user instructions delivered at an input unit operatively coupled to the central computer system.

10. The computerized method as claimed in claim 9, further comprising receiving data in dissimilar formats from at least two imaging instruments and processing the dissimilar format data for display in a standardized format.

11. The computerized method as claimed in claim 9, further comprising receiving an operator voice signal and sending the voice signal to the site of the selected medical imaging instrument.

12. The computerized method as claimed in claim 9, further comprising the central computer system receiving stored data saved earlier locally at one of the medical imaging instruments and presenting the data on the display unit.

13. The computerized method as claimed in claim 9, further comprising the central computer system receiving and recording image data from at least one camera located at an imaging instrument site.

14. A method of claim 9 wherein the central computer system is configured to replicate an operating console of the imaging instrument in response to the control instruction.

* * * * *